US010040736B2

(12) United States Patent
Ravikumar et al.

(10) Patent No.: US 10,040,736 B2
(45) Date of Patent: Aug. 7, 2018

(54) PRODUCTION OF HIGHER ALCOHOLS WITH MINIMUM METHANOL CONTENT FROM THE GASIFICATION OF CARBONACEOUS MATERIALS

(71) Applicant: Fluor Technologies Corporation, Aliso Viejo, CA (US)

(72) Inventors: Ravi Ravikumar, Lancaster, CA (US); Denny Li, Aliso Viejo, CA (US)

(73) Assignee: Fluor Technologies Corporation, Sugar Land, TX (US)

( * ) Notice: Subject to any disclaimer, the term of this patent is extended or adjusted under 35 U.S.C. 154(b) by 369 days.

(21) Appl. No.: 14/836,495

(22) Filed: Aug. 26, 2015

(65) Prior Publication Data
US 2015/0361015 A1    Dec. 17, 2015

Related U.S. Application Data

(62) Division of application No. 13/474,452, filed on May 17, 2012, now Pat. No. 9,149,739.

(51) Int. Cl.
*B01J 8/00* (2006.01)
*C07C 29/151* (2006.01)
(Continued)

(52) U.S. Cl.
CPC ............ *C07C 29/152* (2013.01); *B01D 17/00* (2013.01); *C07C 29/151* (2013.01); *C07C 29/1518* (2013.01); *C07C 29/32* (2013.01); *C10J 3/82* (2013.01); *C10K 1/004* (2013.01); *C10K 1/005* (2013.01); *B01J 2208/00176* (2013.01); *B01J 2208/00256* (2013.01); *C10J 3/466* (2013.01);
(Continued)

(58) Field of Classification Search
CPC ................................ C10J 2300/1665
See application file for complete search history.

(56) References Cited

U.S. PATENT DOCUMENTS 3,064,029 A * 11/1962 White ............... C07C 29/1512
518/725
3,950,369 A *  4/1976 Gent ....................... B01J 8/02
518/705
(Continued)

FOREIGN PATENT DOCUMENTS

| EP | 0253540 A1 | 1/1988 |
| EP | 1916233 A1 | 4/2008 |
| WO | 2005/021421 A2 | 3/2005 |

OTHER PUBLICATIONS

Patent Cooperation Treaty, "Notification of Transmittal of the International Search Report and the Written Opinion of the International Searching Authority, or the Declaration", PCT Application No. PCT/US/13/41698, dated May 17, 2013.

*Primary Examiner* — Jennifer A Leung
(74) *Attorney, Agent, or Firm* — Conley Rose, PC

(57) ABSTRACT

Systems and methods for generating higher alcohols from synthesis gas produced from carbonaceous materials are described, which can include a reactor configured to produce an alcohol stream and $CO_2$ from a syngas feed. The alcohol stream can be separated in one or more downstream separators to produce a net reactor product and a methanol stream that can recycled into the reactor. The net reactor product preferably comprises higher-order alcohols such as ethanol, propanol, and butanol.

12 Claims, 4 Drawing Sheets

(51) Int. Cl.
   *C07C 29/152* (2006.01)
   *B01D 17/00* (2006.01)
   *C07C 29/32* (2006.01)
   *C10K 1/00* (2006.01)
   *C10J 3/82* (2006.01)
   *C10J 3/46* (2006.01)

(52) U.S. Cl.
   CPC ...... *C10J 2200/09* (2013.01); *C10J 2300/093* (2013.01); *C10J 2300/0916* (2013.01); *C10J 2300/0943* (2013.01); *C10J 2300/0973* (2013.01); *C10J 2300/1665* (2013.01); *Y02E 50/18* (2013.01); *Y02E 50/32* (2013.01); *Y02P 20/145* (2015.11)

(56) References Cited

U.S. PATENT DOCUMENTS

| | | |
|---|---|---|
| 7,781,490 B2 | 8/2010 | Lattner et al. |
| 2007/0010589 A1 | 1/2007 | Pearson |
| 2007/0259972 A1 | 11/2007 | Lattner et al. |
| 2009/0048354 A1 | 2/2009 | Bell et al. |
| 2009/0069452 A1 | 3/2009 | Robota |
| 2010/0069514 A1 | 3/2010 | Gracey et al. |
| 2010/0175320 A1 | 7/2010 | Schuetzle et al. |
| 2011/0201699 A1* | 8/2011 | Lucas ............ C07C 29/1518 518/702 |

* cited by examiner

PRODUCTION OF HIGHER ALCOHOLS WITH MINIMUM METHANOL CONTENT FROM THE GASIFICATION OF CARBONACEOUS MATERIALS

This application is a divisional application of, and claims priority to, U.S. application Ser. No. 13/474,452, filed May 17, 2012.

FIELD OF THE INVENTION

The field of the invention is mixed alcohol production and methods related thereto.

BACKGROUND

Ethanol and higher carbon alcohols are utilized as additives in fuel or as feedstocks in the production of other chemical end products. However, the production of alcohols such as ethanol on an industrial scale typically utilizes fermentation processes that require significant amounts of plant feedstock.

In an attempt to reduce the amount of plant feedstock required, the Department of Energy has directed research in the development of liquids from low-cost feedstocks such as biomass and coal in their research laboratories. In 2003, the National Renewable Energy Laboratory (NREL) commissioned a report on the production of ethanol and mixed alcohols via gasification of cellulosic biomass. Studies similar to that described in the NREL report have also been conducted by the Pacific Northwest National Laboratory (PNNL), which has focused its research on the use of biomass in the production of various end products such as transportation fuels and energy production.

Although WIPO pat. publ. no. 2005/021421 to Pearson Technologies, Inc. (publ. March 2005) and U.S. pat. publ. no. 2007/0010589 to Pearson (pub. January 2007) discuss the conversion of syngas into mixed alcohols, these applications are narrowly focused on the use of different catalysts for their specific processes. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

U.S. Pat. No. 7,781,490 to Lattner, et al. discusses the formation of crude methanol for production of olefins. However, Lattner fails to contemplate processes to produce ethanol and higher-order alcohols. U.S. pat. publ. no. 2010/0069514 to Gracey et al. (publ. March 2010) utilizes a standard reformer and then auto-reformer to convert feedstock into syngas. However, such process is limited to the use of natural gas (methane) as a feedstock.

While U.S. pat. publ. no. 2010/0175320 to Schuetzle et al. (publ. July 2010) devises a system optimized to produce fuel gases such as methane, such system fails to appreciate the use of a methanol recycle loop to increase the yield of higher-order alcohols.

U.S. pat. publ. no. 2009/0048354 to Bell, et al. (publ. February 2009) goes a step further and discusses a system having a methanol generation step that recycles gases back to the very beginning of the process. However, Bell fails to contemplate the use of a $CO_2$ removal unit upstream of the reactor.

Thus, there is still a need for systems and methods for producing higher alcohols from synthesis gas produced from carbonaceous materials and having a methanol recycle loop.

SUMMARY OF THE INVENTION

The inventive subject matter provides apparatus, systems and methods in which one can generate higher-order alcohols (e.g., ethanol, propanol, and butanol) from synthesis gas produced from carbonaceous materials. In preferred methods, a carbonaceous feedstock can be reacted in a reactor to produce an alcohol stream and $CO_2$. The alcohol stream can then be separated to produce a net reactor product and a methanol stream. Advantageously, at least a portion of the methanol stream can be fed back to the reactor as a recycle stream to thereby increase eth production of higher-order alcohols while minimizing methanol in the downstream products. Thus, the net reactor product is preferably substantially depleted of methanol.

As used herein, the term "substantially depleted" means less than 10 vol %. Thus, "substantially depleted of methanol" means the stream has less than 10 vol % of methanol.

In some contemplated embodiments, systems can be configured to generate higher-order alcohols from synthesis gas produced from carbonaceous materials. Preferred systems include a gasification system configured to receive a carbonaceous feedstock and produce a syngas feed primarily composed of CO, $H_2$, $CH_4$, and $CO_2$. A reactor can be configured to receive the syngas feed and produce an alcohol stream and $CO_2$, at least a portion of which can be separated in a separator to produce a methanol stream and a product stream. Preferably, at least a portion of the methanol stream can be recycled back to the reactor.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

One should appreciate that the disclosed techniques provide many advantageous technical effects including the production of higher order alcohols such as ethanol, propanol, and butanol as the primary product slate from non-plant feedstock including, for example, biomass or any other low-cost, high-carbon-concentration feedstock such as petroleum coke or coal. In this manner, the cost to produce higher-order alcohols can be significantly reduced, while enabling production of the higher-order alcohols from a wide-range of feedstocks. This advantageously allows facilities to be independent from a single source of feed and thus take advantage of market economics and regulations. In addition, by operating the proposed systems and methods at larger scale sizes can further improve the economics of the process.

Figure 1:
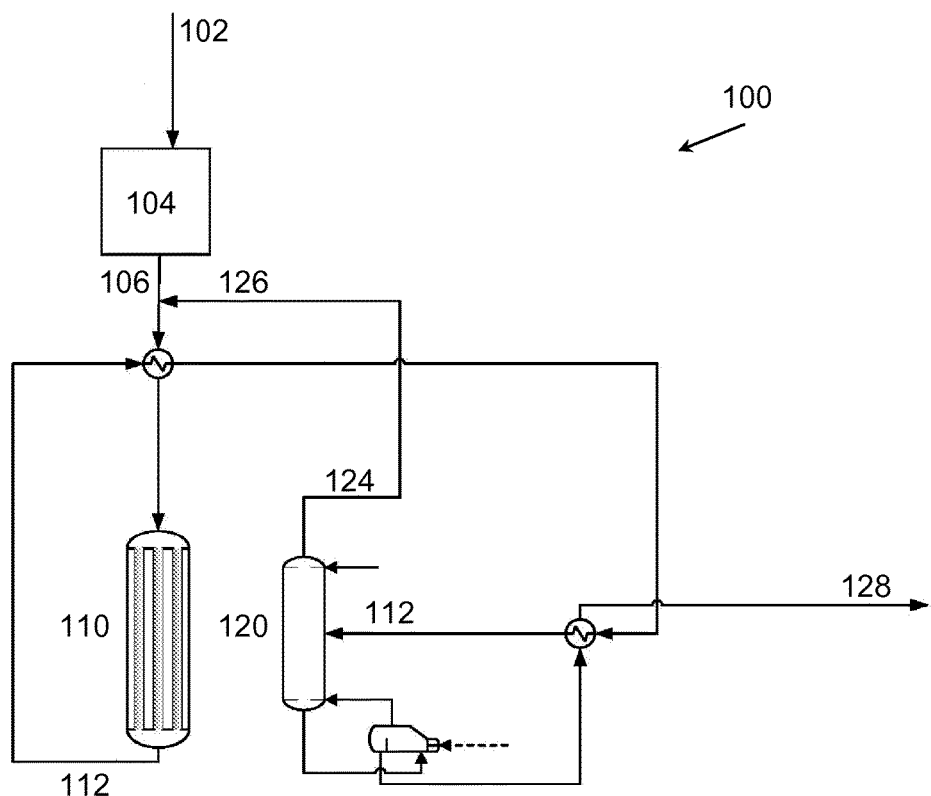
FIGS. 1-3 are schematics of various embodiments of systems configured to generate higher alcohols from synthesis gas produced from carbonaceous materials.
Figure 3:
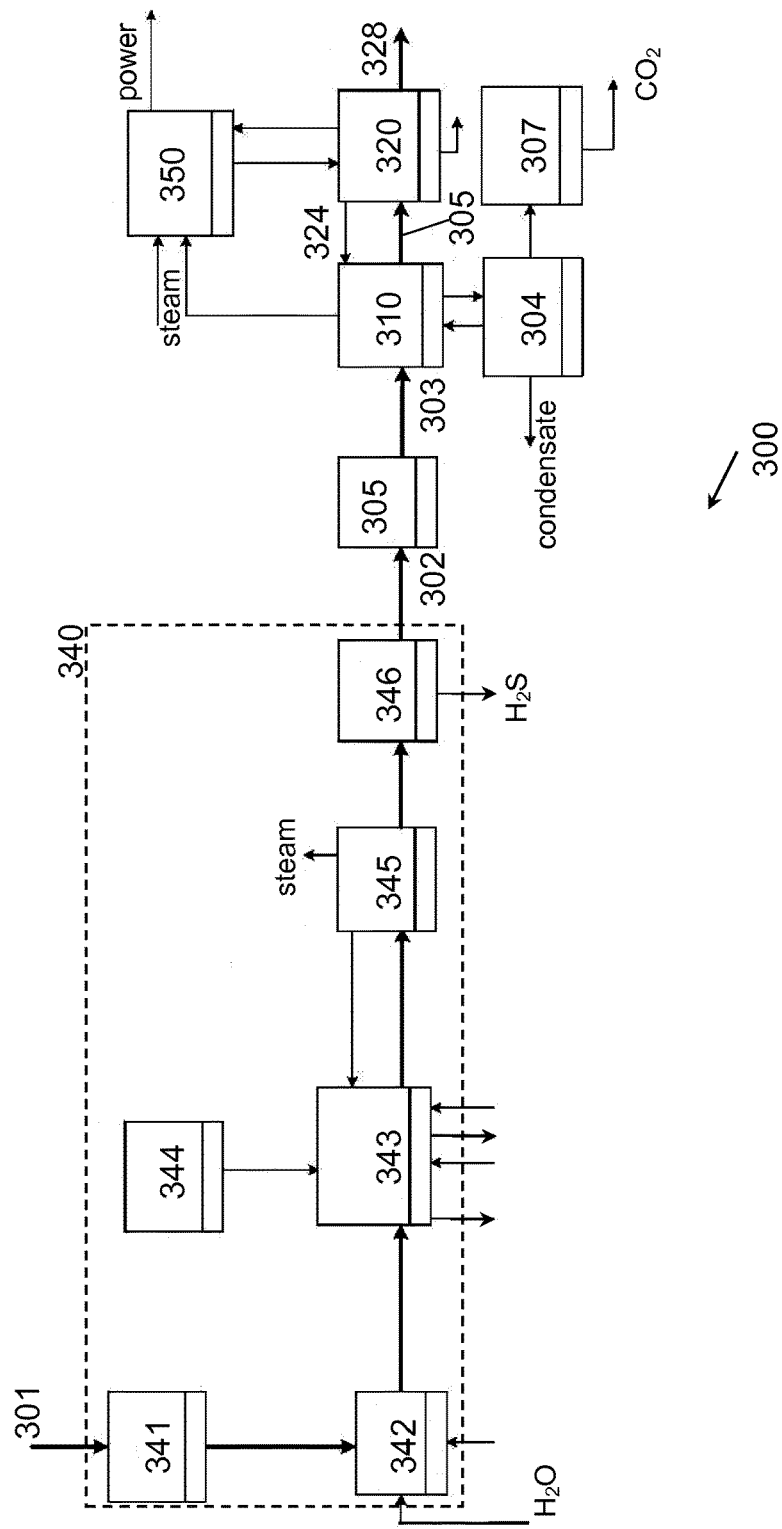

In FIG. 1, a system 100 is shown configured to produce higher-order alcohols from synthesis gas produced from carbonaceous materials. The system 100 preferably receives a syngas feed 102 primarily composed of CO, $H_2$, $CH_4$, and $CO_2$, which is preferably produced in an upstream gasification system (not shown) from a carbonaceous feedstock including, for example, biomass, petroleum coke, and coal. Preferred gasification systems utilize a dry feed gasification process that allows production of syngas from a wide-range of feedstocks including those described above. An exemplary gasification system is shown in FIG. 3.

The syngas feed 102 advantageously can be optionally fed into a $CO_2$ removal unit 104 that is configured to selectively remove $CO_2$ from the syngas feed 102 to produce a first stream 106 that is at least partially depleted, and preferably substantially depleted, of $CO_2$. An exemplary $CO_2$ removal unit is the Fluor Solvent Process developed by Fluor™ Corp., although any commercially suitable process could be used. The removal of $CO_2$ advantageously reduces or eliminates the need for downstream $CO_2$ removal units, and allows system 100 to sequester or capture carbon such as to comply with local regulations.

At least a portion of the first stream 106 can be fed into an alcohol synthesis reactor 110, which is configured to produce a reactor product stream 112 that comprises an alcohol stream and $CO_2$. Alternatively, the syngas feed 102 could be fed directly into reactor 110. The reactor 110 can utilize any commercially suitable catalysts, and the specific catalyst used will depend on the composition of the syngas feed 102 or first stream 106, as well as the desired composition of the reactor product stream 111.

The reactor product stream 112 can then be fed into a downstream separator 120, which is configured to receive at least a portion of the reactor product stream 112, and produce a methanol stream 124 and a product stream 128. It is especially preferred that at least some of the methanol stream 124 is fed back to the reactor 110 as a recycle stream 126. It is contemplated that the recycle stream 126 could be fed directly to reactor 110, or mixed into syngas feed 102 or first stream 106 upstream of the reactor 110. In this manner, the less desired methanol can be recycled to minimize methanol in downstream product streams while increasing the production of higher-order alcohols, when compared with a single pass development lacking methanol and/or syngas recycling loops. In some contemplated embodiments, the methanol stream 124 can include at least some ethanol.

The product stream 128 is substantially depleted of methanol, and can include higher order alcohols. Preferably, the product stream 128 primarily comprises ethanol, propanol, and butanol. In especially preferred embodiments, the product stream 128 comprises less than 5 vol % of methanol, and even more preferably, less than 1 vol % of methanol.

Figure 2:
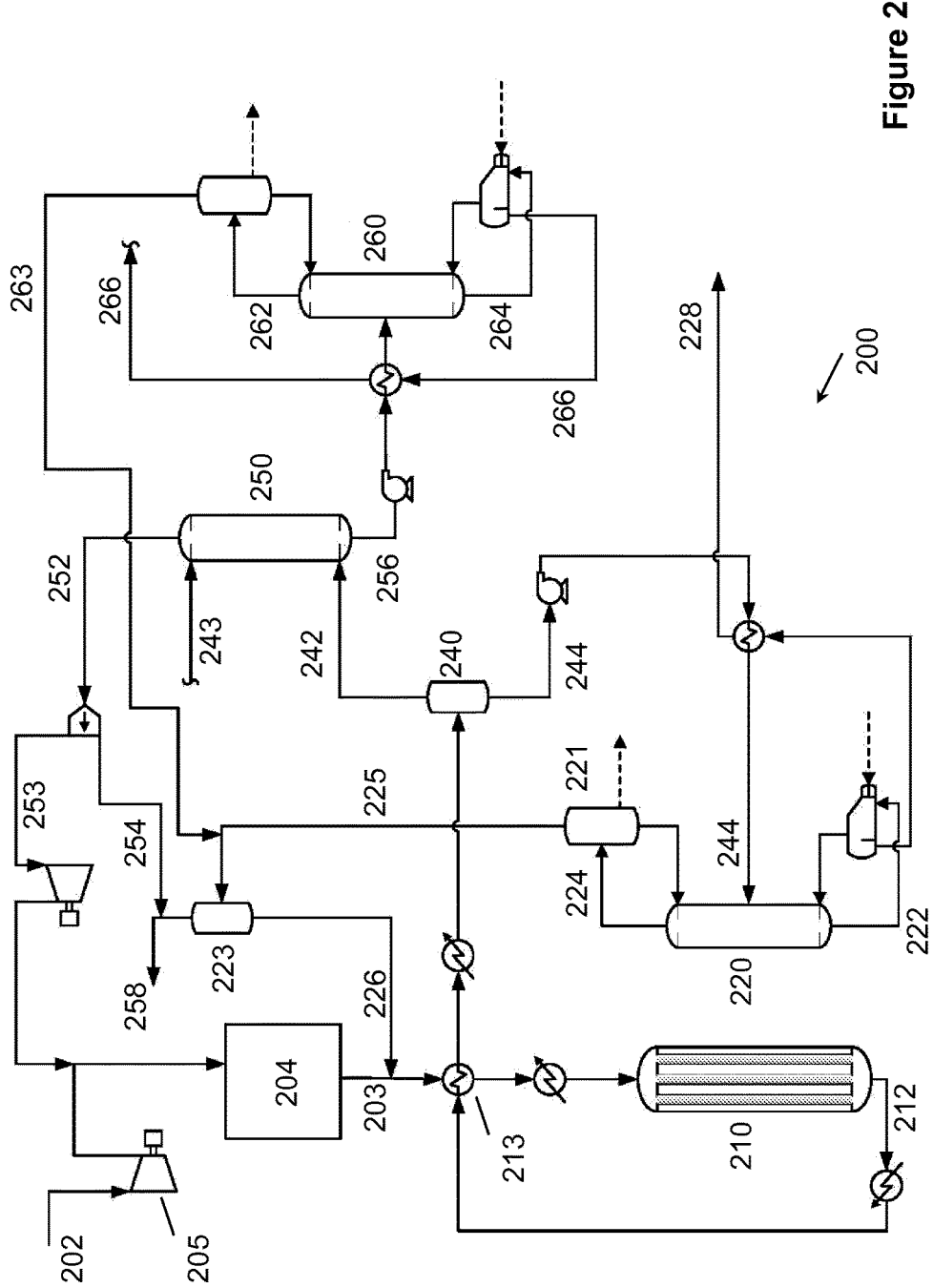

FIG. 2 illustrates a more complex system 200 for generating higher-order alcohols from synthesis gas 202 produced from carbonaceous materials. The syngas 202 can be fed into a compressor 205 where the syngas 202 is compressed before some or all of the syngas 202 is fed into a $CO_2$ removal unit 204. The $CO_2$ removal unit 204 is advantageously configured to selectively remove $CO_2$ from the syngas 202, and the resulting stream 203 can be fed into an alcohol synthesis reactor 210. Optionally, the stream 203 can be passed through one or more heat exchangers to thereby heat the stream 203 as necessary upstream of the reactor 210.

Reactor 210 receives stream 203 and preferably produces a reactor product stream 212 that includes an alcohol stream and $CO_2$. Advantageously, the product stream 212 can be passed through exchanger 213, where excess heat from the product stream 212 can be used to cool the product stream 212, while heating the stream 203 produced by the $CO_2$ removal unit 204.

It is contemplated that some or all of the product stream 212 can be fed into a separator 240, which is configured to produce a bottom product stream 244 comprising methanol and ethanol, and a syngas stream 242 comprising $H_2$, CO, and some methanol. The bottom product stream 244 can be fed into an alcohol separation unit 220 where methanol contained in product stream 244 can be separated as a methanol stream 224 from the higher-order alcohols contained in product stream 222. The product stream 222 can be fed into a reflux unit, and the higher-order alcohols can exit system 200 as stream 228. Advantageously, stream 228 can be passed through a heat exchanger where the stream 228 can have heat exchange contact with stream 244 and thereby heat stream 244 prior to the stream 244 reaching the separation unit 220.

At least a portion of the methanol stream 224, which may contain some ethanol, can be fed into a separator 221. The resulting methanol stream 225 can be fed into a downstream separator 223 where the methanol can be separated from fuel gas 258 that can be used in a downstream superheater. The remaining methanol stream 226 is preferably recycled upstream of reactor 210 and downstream of the $CO_2$ removal unit 204, such that the recycled stream 226 can be further processed in reactor 210 to increase the production of the higher-order alcohols.

The syngas recycle stream 242 from separator 240 can be fed into a methanol wash unit 250 where methanol can be removed from the syngas recycle stream 242 to produce a cleaned syngas stream 252 and a methanol stream 256. The syngas stream 252/253 can be compressed as necessary and fed upstream of the $CO_2$ removal unit 204 where it is recycled and mixed with syngas feed 202.

The methanol stream 256 from the wash unit 250 can be fed into a methanol/$H_2O$ separation unit 260, where water can be separated from methanol to produce an upper methanol stream 262/263, which can be joined with methanol stream 225 to thereby increase the amount of methanol recycled within system 200 and the overall production of higher order alcohols. Condensate produced within separator 260 can exit as stream 264/266, where it can optionally pass through a bottom reflux unit before being repurposed elsewhere. With respect to the remaining numerals in FIG. 2, the same considerations for like components with like numerals of FIG. 1 apply.

In FIG. 3, another embodiment of a system 300 for generating higher alcohols from synthesis gas 302 produced from carbonaceous materials 301 is shown. The carbonaceous materials 301 can be fed into a processing unit 340 upstream of an alcohol synthesis reactor 310. The processing unit 340 can include an optional storage unit 341 where excess materials 301 can be stored. The carbonaceous materials 301 can be prepared at slurry preparation unit 342 where the carbonaceous materials 301 can be mixed with water to form a slurry upstream of a gasification unit 343. The water can come from various sources and preferably the water or other liquid is at least partially recycled from downstream processes. Exemplary sources include, for example, recycled sour water, waste water from downstream acid gas removal unit 346, condensate from fractionation unit 320, and any combination(s) thereof. Of course, make-up water could be added as needed.

The slurry can be fed into gasification unit 343, which is preferably configured to receive the slurry, additional liquid such as grey water and recycled condensate, and air to produce a scrubbed syngas stream that can be fed into a hydrolysis unit 345. It is contemplated that the syngas could include, for example, $H_2$, CO, $CO_2$, $CH_4$, $H_2O$, heavy hydrocarbons, and oxygenated compounds. Air can be provided from air separation unit 344 or any other commercially suitable source.

In the hydrolysis unit 345, steam can be produced and some or all of the remaining fluid can be fed into acid gas removal unit 346. It is contemplated that condensate from the hydrolysis unit 345 can be fed to gasification unit 343 as a recycle stream. The acid gas removal unit 346 can be configured to selectively remove $H_2S$ and produce a syngas feed 302. In this manner, by removing acid gasses upstream of the reactor 310, the reactor 310 and other components downstream of the acid gas removal unit 346 can advantageously be constructed from less costly materials.

The syngas feed 302 can then be fed to the alcohol synthesis reactor 310, which is configured to produce a reactor product stream 305 comprising alcohols and $CO_2$. The reactor product stream 305, or a portion thereof, can then be fed into a fractionation unit 320, where a methanol stream 324 can be separated from the higher order alcohols, and fed as a recycle stream 324 to the reactor 310. A product stream comprising the higher-order alcohols can exit the system 300 as stream 328. Fuel gas from the fractionation unit 320 can optionally be fed into a power generation unit 350. With respect to the remaining numerals in FIG. 3, the same considerations for like components with like numerals of FIG. 1 apply.

Figure 4:
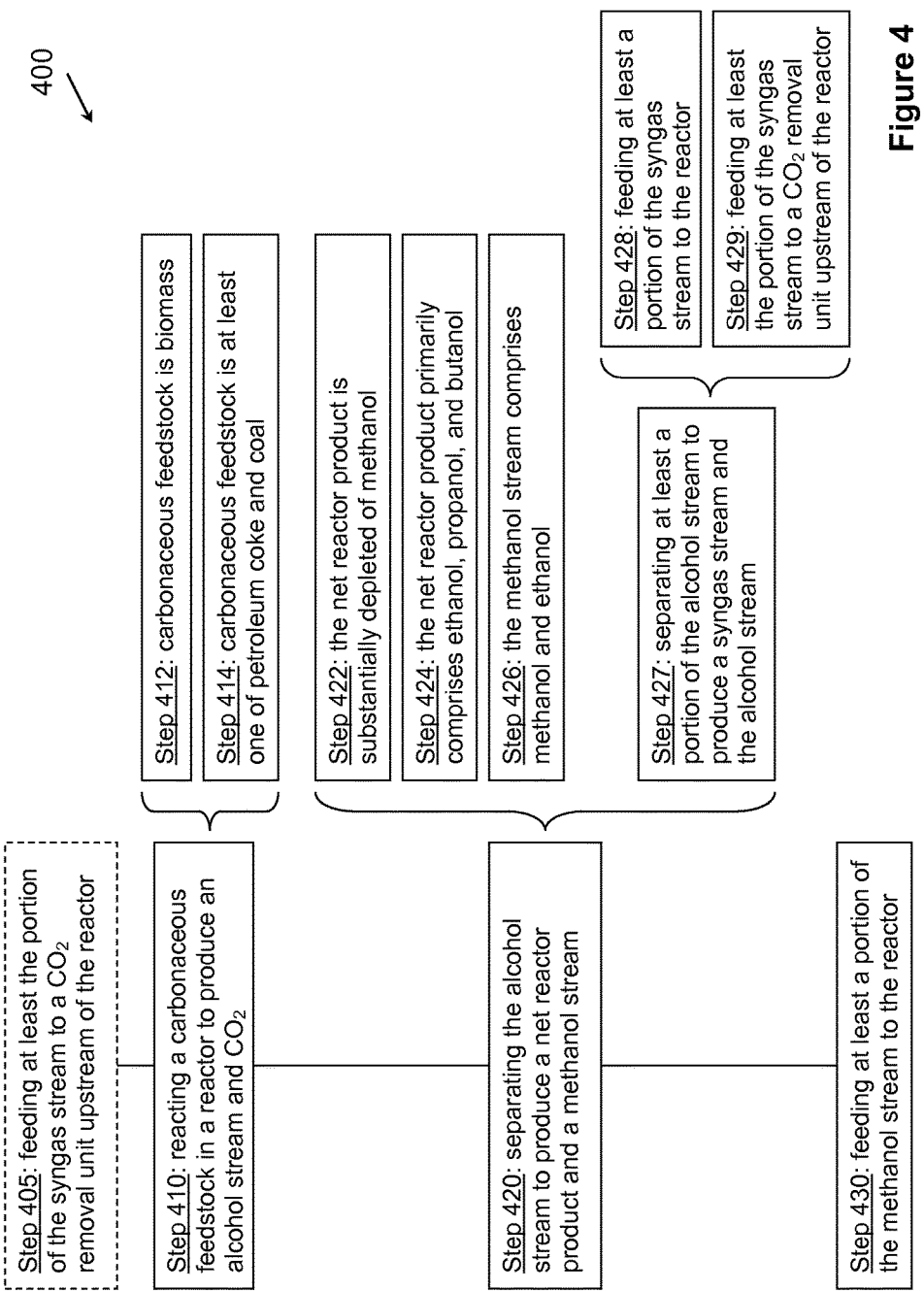
FIG. 4 is a chart of one embodiment of a method for producing higher alcohols from synthesis gas produced from carbonaceous materials.

FIG. 4 illustrates a method 400 for producing higher alcohols from synthesis gas produced from carbonaceous materials. Step 410 can include reacting a carbonaceous feedstock in a reactor to produce an alcohol stream and $CO_2$. In step 412, the carbonaceous feedstock can comprise biomass, while in step 414, the carbonaceous feedstock can comprise at least one of petroleum coke and coal.

The alcohol stream can be separated in step 420 to produce a net reactor product and a methanol stream. Preferably, the net reactor product is substantially depleted of methanol (step 422), and it is especially preferred that the net reactor product primarily comprises ethanol, propanol, and butanol (step 424). In step 426, the methanol stream can include methanol and ethanol.

In step 430, at least a portion of the methanol stream can be fed to the reactor. This advantageously allows for the less preferred methanol to be recycled, while increasing the production of higher-order alcohols.

Optionally, in step 405, $CO_2$ can be selectively removed in a $CO_2$ removal unit upstream of the reactor. In such embodiments, the recycled methanol stream is preferably fed upstream of the reactor and downstream of the $CO_2$ removal unit.

In step 427, at least a portion of the alcohol stream can be separated to produce the alcohol stream and a syngas stream, some or all of which can be fed into the reactor in step 428. In step 429, the syngas stream can be fed to a $CO_2$ removal unit upstream of the reactor.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A plant configured to produce higher alcohols from synthesis gas produced from carbonaceous materials, comprising:
   a gasification system configured to receive a carbonaceous feedstock and produce a syngas feed primarily composed of CO, $H_2$, $CH_4$, and $CO_2$;
   a reactor configured to receive the syngas feed and produce an alcohol stream and $CO_2$;
   a first heat exchanger configured to cool the alcohol stream and $CO_2$ using refrigeration content of the synthesis gas;
   a separator configured to receive at least a portion of the alcohol stream and $CO_2$ and produce a methanol stream and a product stream;
   a second heat exchanger configured to heat the alcohol stream and $CO_2$ before reaching the separator using heat content of the product stream; and
   wherein the product stream from the separator is substantially depleted of methanol.

2. The plant of claim 1, wherein the net reactor product primarily comprises ethanol, propanol, and butanol.

3. The plant of claim 1, further comprising a slurry preparation unit upstream of the gasification system; wherein the slurry preparation unit is configured to mix water with the carbonaceous materials to form a slurry; wherein the gasification system is configured to receive the slurry, grey water, recycled condensate, and air to produce a scrubbed syngas stream that can be fed into a hydrolysis unit; wherein the gasification system is further configured to receive carbonaceous feedstock that comprises biomass.

4. The plant of claim 1, further comprising a hydrolysis unit configured to produce steam; wherein the gasification system is configured to receive condensate from the hydrolysis unit; wherein the gasification system is further configured to receive carbonaceous feedstock that comprises at least one of petroleum coke and coal.

5. The plant of claim 1, further comprising an acid gas removal unit configured to remove $H_2S$; wherein the separator is further configured to produce the methanol stream that also comprises ethanol.

6. The plant of claim 1, further comprising a $CO_2$ removal unit fluidly coupled to, and disposed upstream of, the reactor, and wherein the $CO_2$ removal unit is configured to selectively remove $CO_2$ from at least a portion of the syngas feed.

7. The plant of claim 1, further comprising:
a second separator disposed downstream of the reactor and configured to receive at least a portion of the alcohol stream and produce a syngas stream and the alcohol stream; and
wherein the reactor is further configured to receive at least a portion of the syngas stream.

8. The plant of claim 7, further comprising a $CO_2$ removal unit fluidly coupled to, and disposed upstream of, the reactor, and wherein the $CO_2$ removal unit is configured to receive at least some of the syngas stream.

9. The plant of claim 7, further comprising a methanol wash unit fluidly coupled to, and disposed downstream of, the second separator, and wherein the methanol wash unit is configured to receive at least some of the syngas stream to produce a cleaned syngas stream and a methanol/$H_2O$ stream.

10. The plant of claim 9, further comprising a methanol/$H_2O$ separation unit fluidly coupled to, and disposed downstream of, the methanol wash unit, and wherein the methanol/$H_2O$ separation unit is configured to receive the methanol/$H_2O$ stream and produce a condensate stream and a second methanol stream.

11. The plant of claim 10, wherein the reactor is further configured to receive at least a portion of the methanol stream and the second methanol stream.

12. The plant of claim 1, wherein the reactor is further configured to receive at least a portion of the methanol stream.

* * * * *